United States Patent [19]

Breland

[11] Patent Number: 4,771,859

[45] Date of Patent: Sep. 20, 1988

[54] HEARING AID APPARATUS

[76] Inventor: Thomas Q. Breland, P.O. Box 1838, Gonzales, La. 70737

[21] Appl. No.: 49,544

[22] Filed: May 14, 1987

[51] Int. Cl.$^4$ .............................................. G10K 11/28
[52] U.S. Cl. ...................................... 181/136; 181/129
[58] Field of Search ........................ 181/133, 136, 129

[56] References Cited

U.S. PATENT DOCUMENTS

| 656,182 | 8/1900 | Ehrhardt | 181/136 |
|---|---|---|---|
| 3,139,150 | 6/1964 | Weil | 181/136 |
| 3,513,937 | 5/1970 | Robinson et al. | 181/129 |
| 3,618,698 | 11/1971 | McCabe | 181/136 |
| 3,938,616 | 2/1976 | Brownfield | 181/136 |

FOREIGN PATENT DOCUMENTS 535095  7/1930  Fed. Rep. of Germany ...... 181/136

Primary Examiner—B. R. Fuller
Attorney, Agent, or Firm—Leon Gilden

[57] ABSTRACT

A hearing aid apparatus comprises a pair of cup shaped members positionable behind the ears of a user and being connected by means of a headband. The cup shaped members form sound reflective surfaces which direct sound waves into the user's ears to thus increase his or her hearing capacity. A modified embodiment of the invention utilizes foam padding in a rear portion of the cup shaped members, and this padding causes a gentle forward bending of the user's ears to further increase hearing ability. Additionally, the cup shaped members may be provided with through-extending apertures which permit limited air flow within the members. The air flow through the apertures prevents humidity and heat buildup within the members which could affect sound reflection capabilities. The apertures are of a cone shape with the large open end directed towards the interior sections of the members.

1 Claim, 2 Drawing Sheets

HEARING AID APPARATUS

BACKGROUND OF THE INVENTION

1. Field of the Invention

The present invention relates to hearing aids, and more particularly pertains to a new and improved hearing aid apparatus designed to reflect sound waves towards a user's ears.

2. Description of the Prior Art

The use of mechanical sound amplifiers to reflect sound waves into a user's ears is well known in the prior art. An early form of such sound amplification is present in hand held trumpets or funnels which include a large open end for capturing sound waves and a necked down narrow end which is insertible in a user's ear.

The same technology is to be found in U.S. Pat. No. 3,513,937, which issued to Robinson et al on May 26, 1970, wherein enlarged replicas of human ears are retained on a headband and are positionable over a user's ears. The enlarged ears effectively comprise sound reflective surfaces which greatly enhance the user's hearing capacity. The Robinson et al device operates in the manner of the aforementioned trumpet or funnel inasmuch as a large sound reflective surface is designed to capture sound waves and reflect them through a narrowed passageway leading into the user's ear.

Another mechanical sound amplifier of interest is to be found in German Offenlegungsschrift DE No. 3410388A1 which was published on Sept. 26, 1985. The device shown in this publication includes a hollow body which has an open front end facing a sound source and a closed rear end, along with an outlet opening facing an entry opening of a human ear. The body of the device converges conically towards its rear end, and two such devices are connected by means of a headband so they can be fixedly retained behind a user's ears.

While being functional for its intended purpose, the German mechanical sound amplifier does possess certain disadvantages. For example, its elongated conical shape is not ideally designed for continued air flow, and as such, heat and humidity accumulation could actually cause garbled sound amplification to a user. Further, no means are provided for sealingly and comfortably positioning the device proximate a user's ears, while maximum efficiency is also denied by the failure to position the user's ears in an efficient position relative to the amplifier.

Accordingly, there appears to be a continuing need for new designs of mechanical sound amplification devices wherein the above-discussed disadvantages could be overcome, and in this respect, the present invention substantially fulfills this need.

SUMMARY OF THE INVENTION

In view of the foregoing disadvantages inherent in the known types of mechanical sound amplification devices now present in the prior art, the present invention provides an improved mechanical hearing aid apparatus which permits the use of sound reflective surfaces proximate a user's ears, while also gently aligning and positioning the user's ears so as to obtain maximum hearing improvement. As such, the general purpose of the present invention, which will be described subsequently in greater detail, is to provide a new and improved hearing aid apparatus which has all the advantages of the prior art hearing aid apparatuses and none of the disadvantages.

To attain this, the present invention provides for a pair of cup shaped sound reflective devices which are positionable behind a user's ears through the use of an attached headband. The devices are of a cup or dish shaped construction similar to a dish antenna surface so as to provide for ungarbled sound reflection, and the edges of the devices are provided with a compressible foam material to provide comfort and a sealing effect when the invention is in contact with a user's head. Interior portions of the cup shaped members may be provided with a layer of foam rubber. This rearwardly positioned foam rubber is abuttable with a user's ear and gently forces each ear outwardly and forwardly to thus enhance the natural sound capturing capabilities thereof.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved hearing aid apparatus which has all the advantages of the prior art hearing aid apparatuses and none of the disadvantages.

It is another object of the present invention to provide a new and improved hearing aid apparatus which may be easily and efficiently manufactured and marketed.

It is a further object of the present invention to provide a new and improved hearing aid apparatus which is of a durable and reliable construction.

An even further object of the present invention is to provide a new and improved hearing aid apparatus which is susceptible of a low cost of manufacture with regard to both materials and labor, and which accordingly is then susceptible of low prices of sale to the consuming public, thereby making such hearing aid apparatuses economically available to the buying public.

Still yet another object of the present invention is to provide a new and improved hearing aid apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
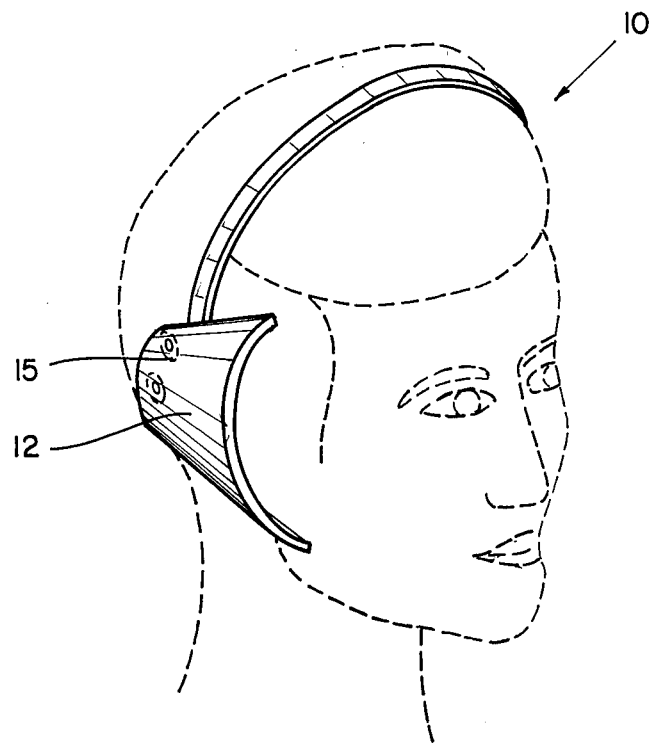
FIG. 1 is a front elevation view of a first embodiment of hearing aid apparatus comprising the present invention.
Figure 2:
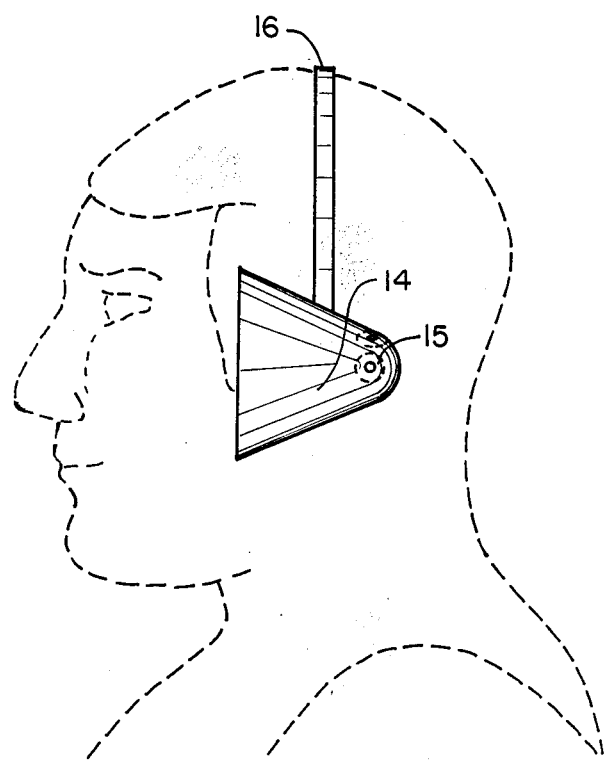
FIG. 2 is a side elevation view of the first embodiment of the invention.

With reference now to the drawings, and in particular to FIGS. 1 and 2 thereof, a new and improved hearing aid apparatus embodying the principles and concepts of the present invention and generally designated by the reference numeral 10 will be described.

More specifically, it will be noted that the hearing aid apparatus 10 essentially comprises a pair of cup or dish shaped members 12, 14 operably positionable behind the ears of a user. The cup or dish shape of the devices 12, 14 allows for the most efficient sound wave reflection to thus eliminate echo and other garbled sound effects. The reflective sound waves are directed into the ears of a user to thus greatly enhance hearing capacity. The cup shaped members 12, 14 are interconnected together by a semirigid flexible headband 16 which operates as a means of retaining the members behind the user's ears.

Positioned within the cup shaped members 12, 14 are a plurality of cone shaped apertures 15 which extend therethrough. These apertures which are located towards a rear closed end portion of each of the cup shaped members 12, 14 facilitate a continual limited air flow through the members, thus to prevent humidity and heat buildup which could otherwise affect sound reflection. The apertures 15 are of a cone shape with the larger open end positioned interiorly of the members 12, 14. This cone shape of the apertures 15 permits a reflection of sound waves back into the interior portions of the members 12, 14 while still permitting the desired air flow.

Figure 3:
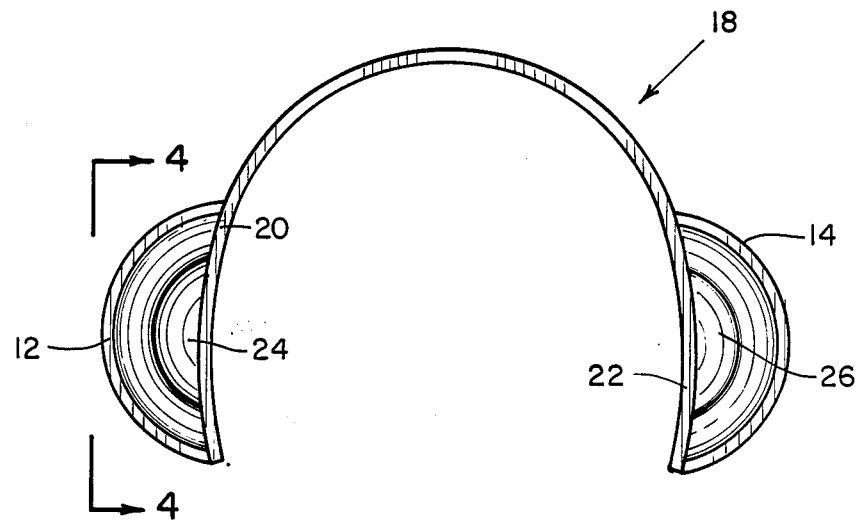
FIG. 3 is a front elevation view of a second embodiment of the invention.
Figure 4:
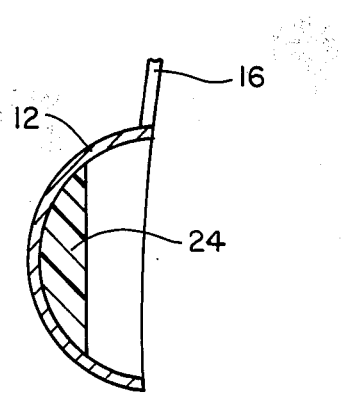
FIG. 4 is a side elevation view, partly in cross section, of the second embodiment of the invention.

A second embodiment of the invention is illustrated in FIGS. 3 and 4 and is generally designated by the reference numeral 18. The modified embodiment 18 recognizes the fact that some type of sealing should be provided between the cup-shaped members 12, 14 and the user's head. This is accomplished by the provision of comfort and sealing strips 20, 22 which are respectively attached to the members 12, 14. The strips 20, 22 provide maximum comfort to the user during a wearing of the embodiment 18 of the invention, while also enhancing the sound reflecting capabilities of the members 12, 14.

Additionally, the second embodiment 18 of the invention recognizes the fact that a user's hearing capability is enhanced when his or her ears are slightly extended outwardly and forwardly. As such, each of the cup shaped members 12, 14 is provided with a respective rearwardly positioned foam rubber pad 24, 26 to achieve this desired positioning of the user's ears. More particularly, the pads 24, 26 will abut against a user's ears during a use of the invention 18, and will effect the desired forward and outward extension of the ear lobes, thereby to further enhance the hearing capabilities of the user.

As to the manner of usage and operation of the present invention, the same should be apparent from the above description. Accordingly, no further discussion relative to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved hearing aid apparatus comprising:

first and second cup shaped members operably positionable behind respective ears of a user, said members serving to reflect sound waves toward said ears;

a headband for connecting said first and second cup shaped members together, said headband also selectively operably retaining said first and second members in a fixed sound receiving and reflecting position proximate said ears;

said headband is constructed from a semi-rigid flexible material, said first and second cup shaped members being attached to opposed ends of said headband;

and further including positioning means for repositioning said user's ears in an outwardly and forwardly extending position when said first and second cup shaped members are operably attached to said user;

wherein said positioning means comprises elongate foam rubber pads positioned within a curvilinear interior portion of said first and second cup shaped members, said pads abutting against an elongate rear portion of said ears to effectively cause said ears to extend outwardly and forwardly thereby to enhance hearing capacity; and sealing means for establishing a sealed and comfortable positioning of said first and second cup shaped members proximate said ears; and further including through extending apertures in said members, said apertures facilitating a flow of air to thus prevent heat and humidity buildup within said members.

* * * * *